United States Patent [19]

Sorensen

[11] Patent Number: 5,263,968
[45] Date of Patent: Nov. 23, 1993

[54] APPARATUS FOR REMOVING PIERCING STUD CLASP

[76] Inventor: David J. Sorensen, 3916 E. 16th St., Vancouver, Wash. 98661

[21] Appl. No.: 905,800

[22] Filed: Jun. 29, 1992

[51] Int. Cl.$^5$ ............................................. A61B 17/00
[52] U.S. Cl. ..................... 606/207; 606/210; 294/99.2
[58] Field of Search ............ 606/188, 205–210; 294/99.2

[56] References Cited

U.S. PATENT DOCUMENTS

| | | |
|---|---|---|
| D. 43,953 | 5/1913 | Allen . |
| D. 286,326 | 10/1986 | Gautam . |
| D. 298,398 | 11/1988 | Trahar . |
| 1,128,135 | 2/1915 | Hammond . |
| 2,818,866 | 1/1958 | Thomas ............................. 606/210 |
| 3,901,243 | 8/1975 | Read ................................. 606/211 |
| 3,916,910 | 11/1975 | Seeling et al. . |
| 4,274,416 | 6/1981 | Sorensen . |
| 4,369,787 | 1/1983 | Lasner et al. ..................... 606/211 |
| 4,572,179 | 2/1986 | Teitelbaum et al. .............. 606/207 |
| 4,610,252 | 9/1986 | Catalano ........................... 606/207 |

Primary Examiner—Stephen C. Pellegrino
Assistant Examiner—William Lewis
Attorney, Agent, or Firm—Steven P. Koda

[57] ABSTRACT

The apparatus engages a piercing stud's clasp, then pushes the stud out of a locked position to ease removal of the clasp. Once out of the locked position, the wearer can pull the clasp and stud from the ear, or remove the clasp while leaving the stud situated in the ear. The apparatus includes a pair of prongs which are inserted through openings in the clasp and a spoon portion which is pushed toward the prongs. The prongs and spoon are pushed toward each other. As a result, the spoon meets the distal end of the stud and pushes the stud from a locked position. An opposing force holds the clasp in place. Removal is accomplished without disturbing the wearer's ear. In particular, the stud is pushed out of the locked position by a force applied at the stud's distal end, rather than pulled out of the locked position by a force applied at the stud's bulbous end. In one embodiment, the apparatus is a pair of thongs having two arms. Prongs extend from one arm, while a hammer portion with a spoon section extends from the other arm.

6 Claims, 5 Drawing Sheets

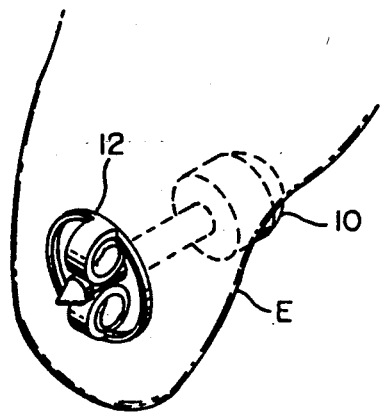
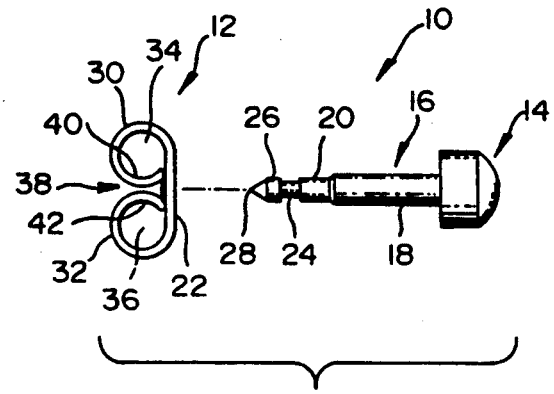
FIG. 1
PRIOR ART
FIG. 2
PRIOR ART
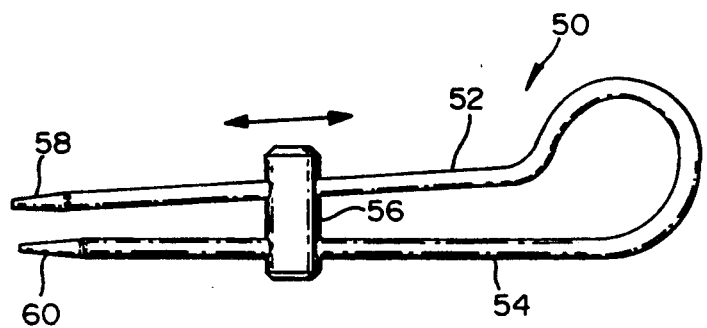
FIG. 3
PRIOR ART

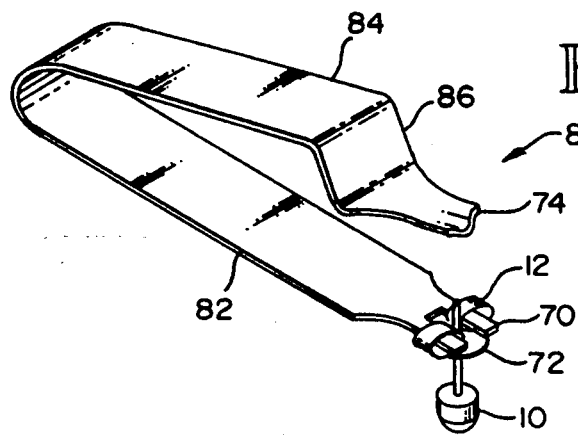
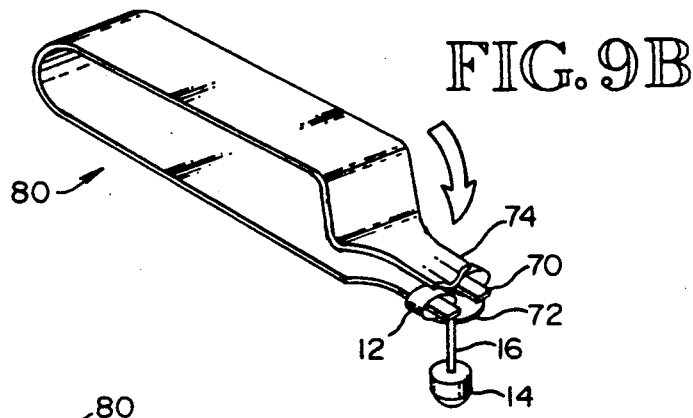
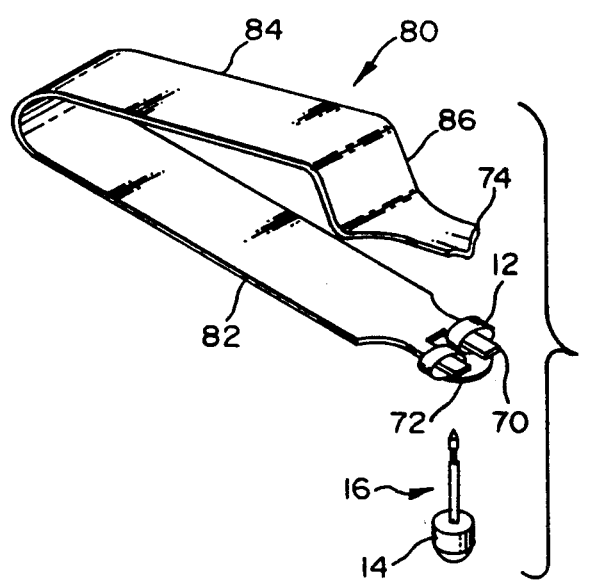

APPARATUS FOR REMOVING PIERCING STUD CLASP

BACKGROUND OF THE INVENTION

This invention relates to tools and apparatus used in the jewelry and earring trade. More particularly, this invention relates to an apparatus for removing an earring clasp from a pierced earring stud.

Pierced earring studs, or piercing studs, are used for creating a channel in an ear lobe for earrings. When a person desires to get an ear pierced, a piercing stud is shot through their ear lobe. An earring clasp then is fastened to the stud to hold the stud in place. FIG. 1 shows a conventional piercing stud 10 held by a conventional clasp 12 as worn on an ear E. Once mounted in a newly pierced ear, the stud is left in place for approximately six weeks allowing a channel to form. After six weeks the stud is removed and the ear is ready for wearing "pierced" jewelry earrings or the like.

Because the stud is to be worn for a prolonged period of time, rather than just for a day, a reliable clasp is needed. Conventional pierced earrings have a clasp which allows the wearer to easily remove the earring. However, a stronger fit is needed for the pierced earring stud to prevent the stud from coming off inadvertently during the six weeks.

If the stud falls off too early, the fatty tissue in the ear lobe may close the channel requiring a new hole to be made in the ear. As the piercing process is uncomfortable and in some cases leads to infection, it is desirable not to repeat the process. It is even more desirable not to repeat the process on the same ear within a short time after piercing the ear.

To provide a secure hold on the piercing stud, the conventional piercing stud clasp has a tight grip. However, the tight grip makes it difficult for the stud clasp to be removed. At the end of six weeks the ear may still be sensitive and manual tugging may irritate the wearer. Accordingly, it is desirable to have a tool which removes the clasp without irritating the wearer.

Manual tugging to remove the clasp is not a controlled motion. During the same motion as the clasp is removed from the stud, the stud inadvertently may be removed from the ear. Even though the stud has been in place for six weeks, it may be undesirable to remove the stud from the channel.

Once the stud is removed from the ear lobe channel, the wearer may have difficulty putting an earring post through the identical channel. It is easy enough to find the channel opening. However, as the post is pushed through and the ear manipulated, the soft fatty tissue of the ear lobe defining the channel may collapse. Specifically, the ear post is straight and rigid, whereas the channel shape changes as the ear lobe is manipulated. Thus, the wearer pushing the post into the channel opening may puncture a hole through the channel wall creating discomfort and risk of infection. One does not want to create a different channel each time a pierced earring is installed. A guide as described in U.S. Pat. No. 4,274,416 allows the piercing stud or any earring post to be removed without losing the channel. The guide fills the channel as the stud is removed. An earring post then fills the channel as the guide is removed. Accordingly, it is desirable to remove the stud clasp while leaving the stud in place.

FIG. 2 shows the conventional earring stud 10 and clasp 12 in detail. The stud 10 has a bulbous portion 14 which is struck to shoot the stud into an ear lobe. The bulbous portion 14 also serves as (1) a grip for holding the stud 10 once inserted in the ear lobe, and (2) an anchor for preventing the stud from passing through to the other side of the ear lobe. Extending from the bulbous portion 14 is a post 16 which extends into and through the ear lobe E. The post 16 has multiple cylindrical sections of varying diameter. A first cylindrical section 18 extends from the bulbous portion 14. Typically section 18 extends through the ear E. A second cylindrical section 20 extends from the first section 16, although at a reduced diameter. Typically, the second section 20 extends from the ear E through the base 22 of clasp 12. A third cylindrical section 24 extends from the second section 20. A fourth section 26 extends from the third section 24 forming a distal end 28. The distal end 28 narrows down toward a point to puncture through the ear lobe as the stud 10 is inserted.

A standard piercing stud has a post 16 which is 0.386 inches long. The first section 18 is 0.26 inches long, having a 0.049 inch diameter. The second section 20 is 0.055 inches long, having a diameter of 0.031 inches. The third section 24 is 0.03 inches long, having a diameter angling down from the second section to a minimum diameter of 0.025 inches, then angling back to a 0.031 inch diameter at the fourth section 26. The fourth section 26 is 0.41 inches long, having a constant diameter of 0.031 inches for the first 0.025 inches, then angling down at 60 degrees to form the distal end 28.

The clasp 12 receives the stud 10 exiting the ear E. The clasp 12 includes a base portion 22. Extending from the base 22 are two wing portions 30, 32. Each wing 30, 32 is a generally rigid structure which folds on itself in a generally circular shape at the base 22 to form a respective opening 34, 36. Although, the wings 30, 32 are shown as a closed circle, the wings need not extend all the way to the base.

The wings 30, 32 fold toward each other. Together they form a clasping structure with a channel opening 38. The stud 10 is inserted through the base 22 into the channel 38 forcing the wings 30, 32 apart in the areas 40, 42. The third portion 24 of stud 10 is of lesser diameter than the adjacent second and fourth sections 20, 26. As the distal end 28, then fourth section 26 progress through the channel 38, the wings areas 40, 42 are driven farther apart. The wings 30, 32, however, are resilient so that when the stud progresses to the lesser diameter third section 24, the wing areas 40, 42 bias back inward decreasing the area of channel 38. The length of the third section 24, the diameter differential between the third section 24 and adjacent sections 20, 26 and the area between wing portions 40, 42 are designed to provide a secure fit in which the clasp 12 holds the stud 10 in place with little play.

A conventional apparatus 50 for removing the piercing stud clasp 12 is shown in FIG. 3. The apparatus 50 spreads the wings 30, 32 of the earring clasp 12 to reduce the hold on the stud 10. The clasp 12 then can be removed from the stud 10 with relative ease. The apparatus 50 includes two arms 52, 54 biased away from each other. A retaining slider 56 receives the two arms and slides along the arms. As the slider moves toward the distal ends 58, 60 the arms spread apart. By carefully controlling the movement of the slider 56 toward the distal ends 58, 60, the channel 38 of clasp 12 is opened as the arms 52, 54 force the wings 30, 32 apart. A problem with this apparatus is that the consumer needs to use caution to prevent the arms 52, 54 from spreading the wings 30, 32 too far apart. If moved too far apart, the wings 30, 32 do not return to their original position. As a result, the opening 38 is permanently increased and the tight grip on the stud 10 is lost. Even with good control of the slider 56, the action on the wings 30, 32, causing opening 38 to increase, reduces the useful life of the clasp 12. Accordingly, another tool for removing piercing stud clasps is needed which is user friendly, reliable, and does not shorten the useful life of the clasp.

SUMMARY OF THE INVENTION

The apparatus of this invention engages a piercing stud's clasp, then pushes the stud out of a locked position to ease removal of the clasp. Once out of the locked position, the wearer can pull the clasp and stud from the ear, or remove the clasp while leaving the stud situated in the ear.

According to one aspect of this invention, the apparatus includes a pair of prongs which are inserted through openings in the clasp and a spoon portion which is pushed toward the prongs. The prongs and spoon are pushed toward each other. As a result, the spoon meets the distal end of the stud and pushes the stud from a locked position while an opposing force holds the clasp in place. More particularly, a force is exerted on the prongs in the direction away from the wearer's ear. Simultaneously, an opposing force toward the wearer's ear is applied at the distal end of the stud. The action of the opposing forces moves the stud relative to the clasp to unlock the stud from the clasp's grip.

According to another aspect of the invention, the apparatus includes two arms. One arm has two extensions (i.e., prongs) fitting into the clasp wing openings. The other arm has an extension forming a hammer or spoon for pushing the stud's distal end part way through the clasp. In one embodiment, the two arms are formed together as thongs.

An advantage of the invention is that the clasp can be removed from a piercing stud without tugging at the clasp and stud. Such manual tugging causes discomfort to the wearer and irritates the ear which is undergoing a healing process from the piercing procedure.

Another advantage is that the clasp is removed without altering the shape or properties of the clasp. In particular, the strength and play in the clasp grip are not altered by the apparatus.

Yet another advantage is that the clasp can be removed while leaving the stud in place. As a result, the clasp can be removed and cleaned, and the area around the ear can be cleaned during the six week forming period. The clasp then is reapplied leaving the stud in place for the remainder of the 6 week period. Another benefit is that the clasp can be removed at the end of the six week period while leaving the stud in place. As a result, a guide can be inserted in the channel as the stud is removed to assure that the newly formed channel is re-used when subsequent jewelry earrings are installed.

The invention will be better understood by reference to the following detailed description taken in conjunction with the accompanying drawings.

BRIEF DESCRIPTION OF THE DRAWINGS

FIG. 1 is a perspective view of an ear portion in which a conventional piercing stud and clasp are mounted for piercing the ear's lobe.

FIG. 2 is an exploded view of the conventional piercing stud and clasp of FIG. 1.

FIG. 3 is a plane view of a conventional earring clasp spreader.

FIGS. 9a–d are perspective views of the FIG. 4 embodiment in operation.

DESCRIPTION OF SPECIFIC EMBODIMENTS

Overview

Figure 4:
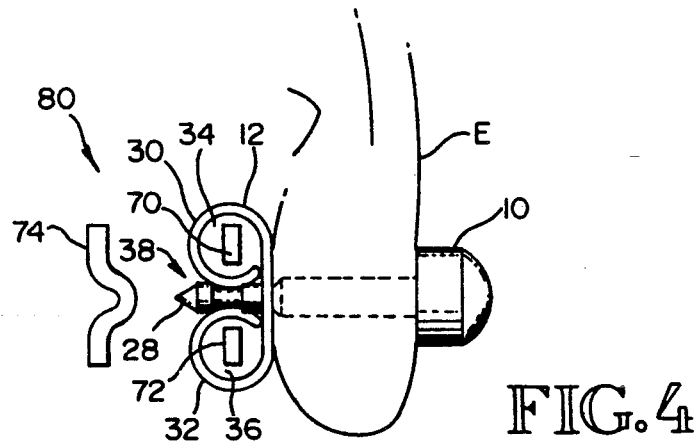
FIG. 4 is a plane view of an ear portion with mounted piercing stud and clasp, along with prongs and spoon portions of an apparatus for removing the clasp according to an embodiment of this invention.

FIG. 4 shows a plane view of an ear portion E having a mounted piercing stud 10 and clasp 12 for piercing an ear. Also shown are prong portions 70, 72 and a spoon portion 74 of an apparatus 80 for separating the clasp 12 and stud 10. The prongs 70, 72 fit into openings 34, 36 defined by respective wing portions 30, 32 of clasp 12. The spoon portion 74 pushes the distal end 28 of the stud 10 through the channel 38 between the wing portions 30, 32, while the prongs 70, 72 exert an opposing force on the clasp 12. The opposing forces push the stud 10 out of a secure, locked position into a released position. Once in the released position, one can easily control movement of the stud 10 and clasp 12 and complete the disassembly.

Tong Embodiment

Figure 5:
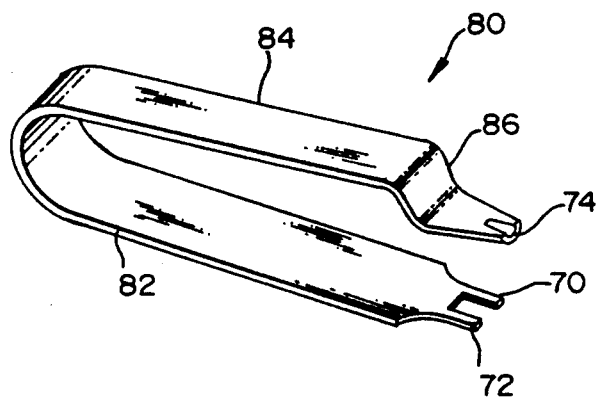
FIG. 5 is a perspective view of an apparatus for removing a piercing stud clasp according to a tong embodiment of this invention.
Figure 6:
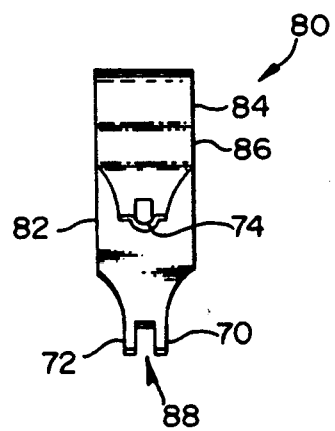
FIG. 6 is another perspective view of the embodiment of FIG. 5.
Figure 7:
FIG. 7 is a perspective view of the embodiment of FIG. 5 in operation.

In the embodiment shown in FIGS. 5, 6 and 7, the prongs 70, 72 and spoon 74 are formed as extensions on opposing arms 82, 84 of a set of tongs 80. The tongs 80 are formed from steel or another generally rigid material. The arms 82, 84 remain apart in a relaxed position as shown in FIG. 4. When opposing forces are applied at each arm, the arms move toward each other causing the spoon portion 74 to approach the prongs 70, 72.

To increase the stiffness of the arm 84, a ridge 86 is formed. A hammer portion 83 extends from one end of the ridge 86. At the end of the hammer portion 83, spoon 74 is formed. The underside of the spoon 74 faces the prongs 72. In one embodiment, the spoon 74 is shaped to extend into an area 88 between the prongs 70, 72. When the spoon 74 and prongs 70, 72 are pushed together, the spoon shape allows the spoon 74 to increase its travel path length by extending between the prongs 70, 72.

Preferably, spoon 74 has a shape, and the prongs 70, 72 have a spacing, designed to allow the spoon 74 to push the stud 10 from the locked position in the clasp 12 without letting the spoon 74 travel a significant distance into channel 38. By having the prongs 70, 72 block the spoon 74 from traveling too far into the area 88 and opening 38, the spoon 74 does not deform the clasp wings 30, 32.

In one embodiment The tongs 80 are formed from a single 5 inch long, 0.5 inch wide, 0.04 inch thick piece of aluminum. The piece is bent at a center length to a 0.25 inch radius so as to form two arms 82, 84. The prongs 70, 72 are formed on one arm 82. Each prong is 0.375 inches long and 0.125 inches wide. The space between the prongs is 0.1 inches wide. The ridge 86 is formed on the arm 84. The ridge 86 extends 0.425 inches at an angle of 110 degrees from the rest of the arm 84. The hammer portion 83 bends back from the ridge 86 extending for a length of 0.325 inches from the ridge 86. The spoon 74 formed on the hammer portion is 0.15 to 0.255 inches long, 0.25 inches wide and 0.09 inches deep having a 0.04 inch radius. In the relaxed state the tong 80 has a spacing of 0.225 inches between the prongs 72 and spoon 74.

Operation

Figure 8A:
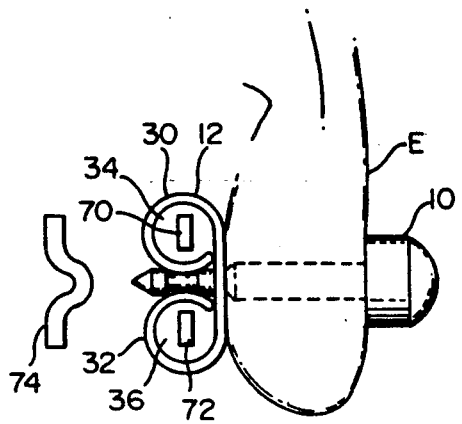
FIGS. 8a–d are diagrams illustrating the action of removing the piercing clasp of FIG. 4.

FIG. 8a-d and 9a-c show the operation of the apparatus 80. In FIG. 8a and 9a the piercing stud 10 is mounted in the ear E and secured by clasp 12. The stud 10 is in the locked position. The prongs 70, 72 are shown inserted in openings 34, 36 defined by the wing portions 30, 32 of the clasp 12. The spoon 74 is in the relaxed position away from the prongs 70, 72.

Figure 8B:
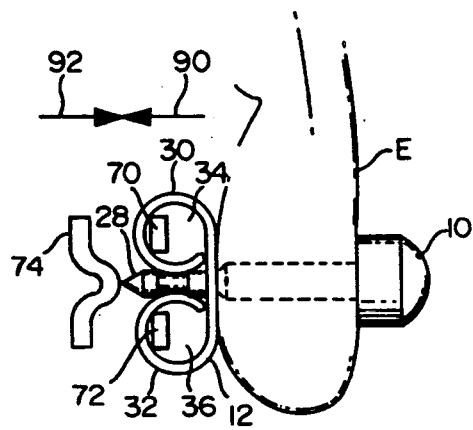
Figure 8C:
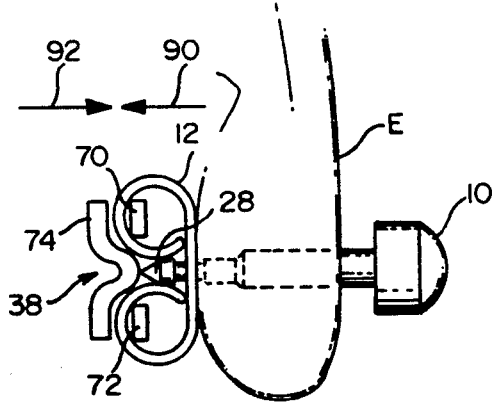

In FIG. 8b the spoon 7 is moved to the distal portion 28 of the stud 10 by applying opposing forces 90, 92 to the prongs 70,72 and spoon 74, respectively. In FIG. 8c and 9b force 92 is increased pushing the stud 10 relative to the clasp 12 out of the locked position. The stud is pushed out of a locked position from the stud's distal end, rather than being pulled out of the locked position from the stud's bulbous end. In particular, the spoon 74 pushes the distal end 28 into channel 38. The distal end 28 is angled. Once the end 28 is pushed sufficiently into the channel 38, the biasing force of the wings 30, 32 contributes to the action of pushing the stud 10 out of the looked position.

The spoon 74 has an undersurface area which is contoured. When forces are applied at the arms 82, 84, the spoon 74 undersurface area extends into the clasp channel 38. In one embodiment, the undersurface is generally contoured to the contours of the wing portions 30, 32 allowing a travel path to the channel 38 opening or into the channel 38. The wing portions 30, 32 limit the travel path of the spoon 74 in the channel 38. The travel path, however, is sufficiently long to push the distal end 28 of the stud 10 out of the locked position.

Figure 8D:
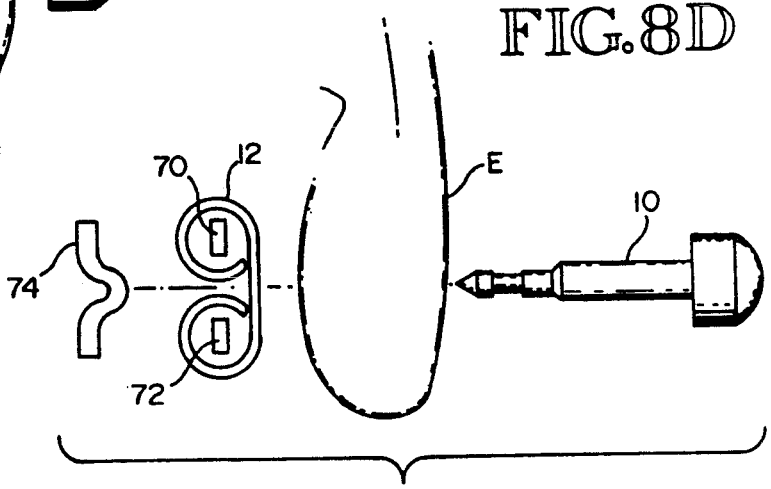

FIG. 8d and 9c show the stud 10 separate from the clasp 12 and the spoon 74 returned to the relaxed position. Once the stud 10 is pushed out of the locked position, the prongs 70, 72 and arm 82 are manipulated to remove the clasp 12 from the stud 10.

Although the stud 10 is shown removed from the ear E, the final separation can also result in the clasp 12 being removed, while the stud 10 remains in the ear E.

Alternative Embodiments

Although a preferred embodiment of the invention has been illustrated and described, various alternatives, modifications and equivalents may be used. For example, although arms 82, 84 are joined in a tong embodiment, the arms also may embody levers in a scissor-like embodiment. Further, the arms may be of varying length, shape and size. Also, although the spoon 74 is shown having an indented upper surface and contoured lower surface, the upper surface need not be of any particular shape. It is the shape of the lower portion which allows a travel path length into channel 38 so as to push the stud 10 out of the locked position. Therefore, the foregoing description should not be taken as limiting the scope of the inventions which are defined by the appended claims.

What is claimed is:

1. An apparatus for removing a clasp from a piercing stud, the clasp having two wing portions with respective openings, the wing portions defining a channel, the stud having a distal end, the stud held by the clasp in a locked position within a channel, comprising:

first prong means for extending through one of the clasp openings and a second prong means for extending through the other of the clasp openings, the first prong means being fixed relative to the second prong means; and means for contacting the distal end of the stud to push the stud relative to the clasp channel, the contacting means comprising a spoon having a contoured non-planar undersurface;

wherein a first force applied through said first and second prong means and a second opposing forces applied through said contacting means cause the stud to be pushed from the locked position facilitating removal of the clasp, the spoon extending into the channel when said first and second forces are applied, travel of the spoon into the channel being limited by contours of the clasp wing portions.

2. The apparatus of claim 1 comprising a first arm and a second arm;

the first arm comprising said first and second prong means;

the second arm comprising said contacting means; and wherein said first and second forces are applied at said first and second arms, respectively.

3. The apparatus of claim 2 in which said first arm and said second arm are coupled together.

4. The apparatus of claim 3 in which said first arm and said second arm are integrally formed.

5. A piercing stud and clasp, and an apparatus for removing the clasp from the piercing stud, the clasp having two wing portions with respective openings, the wing portions defining a channel, the stud having a distal end, the stud held by the clasp in a locked position within the channel, the removing apparatus comprising:

(a) a first arm having first prong means for extending through one of the clasp openings and second prong means for extending through the other of the clasp openings, the first prong means being fixed relative to the second prong means; and (b) a second arm comprising an extended portion, a ridge for increasing the stiffness of the second arm, and a hammer portion for contacting the distal end of the piercing stud to push the stud relative to the clasp channel, the hammer portion comprising a spoon having a contoured non-planar undersurface;

(c) wherein a first force applied through said first and second prong means and a second opposing force applied through said hammer portion cause the stud to be pushed from the locked position, facilitating removal of the clasp, the spoon extending into the channel when said first and second forces are applied, travel of the spoon into the channel being limited by contours of the clasp wing portions.

6. A method for removing a piercing clasp from a piercing stud, the clasp having two wing portions with respective openings, the wing portions defining a channel, the stud having a distal end, the stud held by the clasp in a locked position within the channel, the method comprising the steps of:
  applying a first force at a first arm having first prong means for extending through one of the clasp openings and second prong means for extending through the other of the clasp openings, the first prong means being fixed relative to the second prong means; and
  simultaneously applying a second opposing force at a second arm, the second arm having a hammer portion for contacting the distal end of the piercing stud, the hammer portion comprising a spoon having a contoured non-planar undersurface; and
  wherein the two forces cause the spoon to extend into the channel between the clasp wing portions forcing the wing portions apart and pushing the stud from the locked position, facilitating removal of the clasp, and wherein travel of the spoon into the channel is limited by contours of the clasp wing portions.

* * * * *